United States Patent
Buijs et al.

(10) Patent No.: US 6,194,572 B1
(45) Date of Patent: Feb. 27, 2001

(54) PROCESS TO PREPARE ε-CAPROLACTAM

(75) Inventors: Wim Buijs, Schinnen; Henricus F. W. Wolters, Echt; Rudolf P. M. Guit, Maastricht; Frank P. W. Agterberg, Susteren, all of (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/376,310

(22) Filed: Aug. 18, 1999

Related U.S. Application Data

(60) Provisional application No. 60/040,379, filed on Mar. 10, 1997.

(30) Foreign Application Priority Data

Feb. 19, 1997 (EP) ................................................. 97200481

(51) Int. Cl.$^7$ ................................................. C07D 201/08
(52) U.S. Cl. ............................................ 540/538; 540/539
(58) Field of Search ...................................... 540/538, 539

(56) References Cited

U.S. PATENT DOCUMENTS

| | | | |
|---|---|---|---|
| 3,658,810 | 4/1972 | Tanaka | 260/239.3 |
| 4,599,199 | 7/1986 | Fuchs | 260/239.3 |
| 4,730,040 | 3/1988 | Vagt et al. | 540/538 |
| 4,963,673 | * 10/1990 | Merger et al. | 540/538 |
| 5,693,793 | 12/1997 | Ritz et al. | 540/539 |

FOREIGN PATENT DOCUMENTS

| | | |
|---|---|---|
| 22 49 993 | 4/1973 | (DE) . |
| 38 43 793 | 7/1990 | (DE) . |
| 729 943 | 9/1996 | (EP) . |
| 1184282 | 7/1959 | (FR) . |

* cited by examiner

*Primary Examiner*—Bruck Kifle
(74) *Attorney, Agent, or Firm*—Pillsbury Winthrop LLP

(57) ABSTRACT

Process to prepare ε-caprolactam by treating 6-aminocaproic acid, 6-aminocaproate ester or 6-aminocaproamide or mixtures comprising at least two of these compounds in the presence of superheated steam in which a gaseous mixture comprising ε-caprolactam and steam is obtained, wherein the process is carried out in the absence of a catalyst at a temperature between 250 and 400° C. and at a pressure of between 0.5 and 2 MPa. The invention also encompasses a process to prepare ε-caprolactam starting from 6-aminocapronitrile by performing a hydrolysis and a subsequent step as described above.

12 Claims, No Drawings

PROCESS TO PREPARE ε-CAPROLACTAM

This application claims the benefit of U.S. Provisional Application No. 60/040379, filed Mar. 10,1997.

The invention relates to a process to prepare ε-caprolactam by treating 6-aminocaproic acid, 6-aminocaproate ester or 6-aminocaproamide or mixtures comprising at least two of these compounds in the presence of superheated steam in which a gaseous mixture comprising ε-caprolactam and steam is obtained.

Such a process is described in U.S. Pat. No. 3,658,810. This patent publication describes a process to prepare ε-caprolactam by treating 6-aminocaproic acid, 6-aminocaproamide or mixtures of the two with superheated steam at a temperature from 200–350° C. and a pressure of between 0.05 and 0.5 MPa. The best results are obtained when a non-volatile phosphoric acid-catalyst is also present. The pressure is preferably according to the description between 0.1 and 0.3 MPa. It was presented as an advantage of this process that it could be performed at atmospheric pressure. All the examples illustrating the non-catalyzed process variant were performed at atmospheric pressure.

A disadvantage of this known process is that high yields are only obtainable when the non-volatile phosphoric acid is used. When the process is performed in the absence of a catalyst the highest yield illustrated in the examples of U.S. Pat. No. 3,658,810 is about 74%. The use of non-volatile phosphoric acids is not advantageous because special measures, such as the use of non corrosive reactor material, is needed. Furthermore when 6-aminocaproamide is used as substrate the catalyst will be consumed because ammonium phosphate will be formed.

The object of the present invention is a simple process to prepare ε-caprolactam in a high yield starting from 6-aminocaproic acid, 6-aminocaproate ester and/or 6-aminocaproamide.

This object is achieved in that the process is carried out in the absence of a catalyst at a temperature between 250 and 400° C. and at a pressure of between 0.5 and 2 MPa.

It has been found that with the process according to the invention high yields to ε-caprolactam can be achieved even though no additional catalyst is present. Another advantage is that the activity of the reaction is higher when compared to the activity at atmospheric pressure. Because of the higher activity smaller process equipment can be used.

U.S. Pat. No. 4,599,199 describes a process to prepare ε-caprolactam by treating 6-aminocaproic acid with superheated steam in a fluidized alumina bed at atmospheric pressure. This patent publication teaches a catalyzed process.

Processes to prepare ε-caprolactam starting from 6-aminocaproic acid are for example described in U.S. Pat. No. 4,730,040. In this patent publication a process is described in which 6-aminocaproic acid is converted to ε-caprolactam in the liquid phase in the absence of an additional catalyst at a temperature of 300° C. In such a process a liquid reaction mixture containing ε-caprolactam, unconverted 6-arminocaproic acid and oligomers is obtained. The present invention is different because ε-caprolactam is obtained in the gaseous phase, which phase does not contain substantial amounts of unconverted starting compounds and/or oligomers. This is advantageous because the purification of ε-caprolactam is easier compared to this prior art process.

The process according to the invention is carried out in the absence of a catalyst. By catalyst it is meant homogeneous and heterogeneous catalyst which are present in order to catalyze the reaction as for example illustrated in the earlier mentioned U.S. Pat. No. 3,658,810, which illustrates a homogeneous catalyst and in U.S. Pat. No. 4,599,199, which illustrates a heterogeneous alumina catalyst. It should be clear that a process, in which a negligible amount of a catalyst-like compound is present which compound does not affect the reaction noticably, is a process carried out in the absence of a catalyst according to this invention.

The starting mixtures comprising 6-aminocaproic acid, 6-aminocaproate ester and/or 6-aminocaproamide can be obtained by various processes. For example in U.S. Pat. No. 4,730,040 a process is described in which an aqueous mixture is obtained containing 6-aminocaproic acid and some ε-caprolactam starting from 5-formylvalerate ester. Further in EP-A-729943 a process is described in which an aqueous mixture is obtained containing 6-aminocaproic acid, 6-aminocaproamide and ε-caprolactam also starting from a 5-formylvalerate ester. U.S. Pat. No. 5,068,398 describes a process in which an aqueous mixture is obtained containing 6-aminocaproate ester and some ε-caprolactam starting from a 5-formylvalerate ester.

The starting compounds are preferably 6-aminocaproic acid and/or 6-aminocaproic amide because high yields to ε-caprolactam are possible when starting from this compound. Next to the 6-aminocaproic acid and/or 6-aminocaproamide some ε-caprolactam and/or oligomers of ε-caprolactam, 6-aminocaproic acid and/or 6-aminocaproamide can be present. A typical mixture which can be used as starting mixture for the present invention comprises between 5 and 50 wt % 6-aminocaproic acid, 10 and 50 wt % 6-aminocaproamide, 0 and 40 wt % ε-caprolactam and between 0 and 35 wt % of the ear mentioned oligomers in which the total of these fractions is 100 wt. %.

The 6-aminocaproate ester compound can be represented by the following general formula:

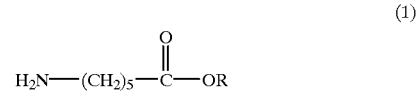

(1)

where R is preferably an organic group with 1 to 20 carbon atoms and more preferably with 1 to 6 carbon atoms. The organic group is an alkyl, cycloalkyl, aryl or aralkyl group. More preferably R is an alkyl group. Examples of R groups include methyl, ethyl, propyl, isopropyl, n-butyl, tert-butyl, isobutyl, cyclohexyl, benzyl and phenyl. By preference R is methyl or ethyl.

Starting mixtures can also be obtained by the method as described below. Processes starting from 6-aminocapronitrile can also yield mixtures comprising 6-aminocaproic acid. Such mixtures can be advantageously used in the process according to the invention. Processes to prepare ε-caprolactam starting from 6-aminocapronitrile are for example described in U.S. Pat. No. 5,495,016. This patent publication describes a process to prepare ε-caprolactam by contacting 6-aminocapronitrile in a cyclization zone with water in the liquid phase at a temperature of about 300° C. at super atmospheric pressure resulting in an aqueous mixture containing ammonia, ε-caprolactam and ε-caprolactam precursors, for example 6-aminocaproic acid, 6-aminocaproic amide and oligomers. The weight ratio oligomers to ε-caprolactam is about 1:3 according to the examples. ε-caprolactam is isolated by distillation. The oligomers can be further converted, according to this patent publication, to ε-caprolactam by either recycling them to the cyclization zone or treating them in a further reactor in a similar fashion as performed in the cyclization zone.

A disadvantage of this process is that high concentration of oligomers are present in the reboilers of the various distillation steps. This can result in fouling due to solidification of the oligomers in pipes and other process equipment. Furthermore ε-caprolactam will polymerize to oligomers under these conditions (2 wt. % of the ε-caprolactam may polymerize according to Example I of U.S. Pat. No. 5,495,016) resulting in a loss of yield per pass.

By (1) contacting 6-aminocapronitrile with water under hydrolysis conditions, (2) separating water and ammonia, which is formed in the hydrolysis reaction, and (3) contacting the resulting mixture with superheated steam according to the process according to this invention, these problems are overcome.

It has been found that with the above described process ε-caprolactam can be obtained starting from 6-aminocapronitrile without the need to recycle or further process the oligomers formed in the process.

The contacting under hydrolysis conditions can be performed in any manner known to one skilled in the art. Under these hydrolysis conditions the nitrile group will react with water to an amide group or a carboxylic acid group and ammonia. Hydrolysis conditions can be achieved by contacting with water in the absence or presence of a hydrolysis catalyst, for example a (Lewis) acid or base as described in for example I. March, Advanced Organic Chemistry, Third ed., Ed. J. Wiley & Sons Inc., 1985, page 788 or in Organic Chemistry, International Student Edition, Second ed. Mc. Graw-Hill Book Company Inc., 1964, page 307.

The hydrolysis reaction can be performed in the liquid phase in the presence of homogeneous catalysts, for example aqueous NaOH optionally containing $H_2O_2$, aqueous $H_2SO_4$, formic acid, HCl or HBr. Preferably heterogeneous catalyst are used in large scale processes. It can be advantageous to contact 6-aminocapronitrile with water in the gas phase, for example when 6-aminocapronitrile is obtained in the gas phase in a previous process step. Possible examples of heterogeneous catalyst are solid acid catalyst, for example silica gel, silica-alumina, supported phosphoric acid, Group III phosphates and sulfates, for example phosphates and sulfates of aluminium, boron and gallium, transition metal oxides, for example one or more oxides of vanadium, chromium, manganese, iron, cobalt and nickel. The catalyst are generally of the type employed for hydration, dehydration and esterfication reactions.

The temperature of the hydrolysis step is preferably between 50 and 400° C. One skilled in the art can easily determine the optimal temperature. The pressure of the hydrolysis step will depend on the chosen mode of operation, i.e. gas or liquid phase process. When the hydrolysis is carried out in the liquid phase in the higher temperature region of 250–400° C. more ε-caprolactam and oligomers of 6-aminocaproamide, 6-aminocaproic acid and/or ε-caprolactam will be formed. An example of such a high temperature/pressure hydrolysis is the uncatalyzed hydrolysis described in the afore mentioned U.S. Pat. No. 5,495,016.

The products formed in the hydrolysis step are for the most part 6-aminocaproamide, 6-aminocaproic acid, ε-caprolactam and/or the above mentioned oligomers.

For the performance of the cyclization step it has been found that it is not critical how the hydrolysis is performed. The different possible compositions of the hydrolysis mixtures obtained in step (1) can all be advantageously further processed in steps (2) and (3) to yield ε-caprolactam.

It can be advantageous to separate ε-caprolactam (if present) from the mixture obtained in step (1) prior to step (3). Separating ε-caprolactam can be performed by for example extraction using for example chloroform, dichloromethane, 1,1,1-trichloroethane, and phenols, like dodecylphenol as extraction agents or $C_5$–$C_{10}$ alcohols, for example 4-methyl-2-pentanol or 2-ethyl-⊕-hexanol.

The hydrolysis step (1) and step (2) can be combined in one step, for example by performing the hydrolysis in the liquid phase and continuously separating water and ammonia from the reaction mixture by evaporation. Another possible embodiment is a reactive distillation, in which the column is packed with heterogeneous hydrolysis (acid or base) catalyst. The top product will be a water/ammonia mixture and the bottom product a hydrolysis mixture according to the process of the invention as can be obtained in step (2).

If step (2) is performed separately then this step is preferably performed by distillation. The pressure at which the distillation is performed is not critical. When step (1) is performed in the gas phase the hydrolysis products of 6-aminocapronitrile can be simply separated from ammonia and steam by for example partial condensation.

The 6-aminocaproic acid or 6-aminocaproamide or mixtures comprising these starting compounds which are obtainable by the above described processes, are preferably contacted with the superheated steam as a liquid, for example as a melt.

At least a part of the water present in the mixtures which are obtainable by the above described processes is preferably removed, for example by distillation at a temperature of 60–160° C., preferably at a temperature of 80–140° C. It has been found that the amount of water in the starting mixture of the process according to the invention is preferably as low as possible.

Preferably the starting compound or mixture of starting compounds is brought into contact with the steam as a liquid mixture containing between 0–50 wt. % water, more preferably between 0–20 wt. % water and between 50–100 wt. % of starting compound(s), more preferably between 80–100 wt. % of starting compounds. The starting compounds can even be fed to the reactor in a finely divided solid form.

The temperature during the contacting with the superheated steam is between 250 and 400° C. and preferably between 270 and 350° C. The pressure is between 0.5 and 2 MPa. Preferably the pressure is below 1.5 MPa. Temperatures higher than 350° C. are more disadvantageous because of the possible occurence of degradation reaction causing yield loss and causing undesirable by-products making the purification more difficult.

Part of the steam can be substituted with an inert stripping gas, for example nitrogen.

In a continuous process the steam-feed ratio (in weight) is preferably between 1 and 20. This feed is the total weight of 6-aminocaproic acid, 6-aminocaproamide, oligomers and ε-caprolactam present in the starting mixture. This feed does not include any water which may be present.

The process is preferably performed as a continuous process in which steam is continuously fed to a reaction zone in which the starting compound is present. More preferably the starting compound or mixture of starting compounds is continuously or semi-continuously fed to the reactor zone as an aqueous mixture, in which the feed has a temperature of between room temperature and the temperature of the reactor zone, preferably the temperature is between 50–150° C.

The continuously operated process according to the invention can be practiced in a reactor apparatus which is provided with an inlet for the starting material, an outlet for the steam/ε-caprolactam product and means for supplying steam such that the steam is contacted with the starting material. The reactor is optionally equiped with a heating device and optionally with a mixing device. To this reactor the starting compound and the steam can be continuously fed. A possible reactor is a fluidized bed reactor containing inert particles in which the bed is kept fluidized by the steam. Another example of a reactor is a horizontal tube reactor having a rotating axis on which axis means for mixing and/or transport are present. Also means are present which prevent fouling of the interior vessel wall and which promote an optimal steam/substrate contact area for masstransfer. Examples of suitable reactors are packed tower-type reactor, one or multiple staged bubble columns or a multi-tube reactor.

The gas phase obtained in the process according to the invention will comprise steam and ε-caprolactam and optionally some ammonia, for example when 6-aminocaproamide is a starting compound. The ε-caprolactam can be isolated from this gaseous stream obtained by the process according to the invention by normal methods known to one skilled in the art, for example as described in U.S. Pat. No. 3,658,810. Preferably ε-caprolactam is isolated by partial condensation in which a liquid aqueous phase containing ε-caprolactam and water and a gaseous phase containing steam is obtained. The steam can be reused in the process according to the invention, for example by first passing steam via a heat exchanger. Preferably any ammonia present is separated before reusing the steam. ε-caprolactam can be isolated from the condensed aqueous mixture by any separation technique, for example distillation or by the above described extraction. The water phase, poor in ε-caprolactam, can be reused in the process. Preferably any ammonia present is separated before reusing the water.

The partial condensation is performed at a temperature of 80–200° C., preferably at a temperature of 100–170° C. It has been found critical that the period of time during which the gaseous mixture leaving the reactor is cooled to the temperature of the partial condensation is as short as possible to reduce yield loss of ε-caprolactam. Preferably the cooling of the reactor mixture is performed within 60 seconds, more preferably within 30 seconds and most preferred within 10 seconds from leaving the reactor.

The ε-caprolactam can subsequently be purified by methods known for purifyung ε-caprolactam obtained by Beckmann rearrangement. An examplary method of purifying ε-caprolactam is described in U.S. Pat. No. 5,496,941.

In one preferred embodiment, the purification of the ε-caprolactam comprises the following steps:
1) contacting ε-caprolactam at from 30 to 80° C. and from 0.1 to 0.5 MPa over an ion exchanger containing terminal acid groups,
2) treating the mixture obtained in step (1) with hydrogen at from 50 to 150° C. and from 0.15–25 MPa in the presence of a hydrogenation catalyst and
3) separating water and other light components by distillation
4) isolating ε-caprolactam by distillation.

The order of the ion exchange step (1) and hydrogenation step (2) can be reversed if desired. Steps (1) and (2) can be optionally performed in water or another solvent. This purification procedure results in ε-caprolactam of very good quality. The ion exchange and hydrogenation treatment are known methods for purifying ε-caprolactam obtained by Beckmann rearrangement and can be performed by these well known methods.

In a second preferred embodiment, the purification of the ε-caprolactam is achieved by crystallization in a process of concentrating. The crystallized ε-caprolactam resulting from concentrating is generally sufficiently pure to be used directly.

The invention will be elucidated with the following non-limiting example.

Example I

A 500 ml autoclave having a turbine mixer was filled with 100 g 6-aminocaproic acid. The autoclave was subsequently flushed with nitrogen and a pressure valve was adjusted such that the pressure in the reactor was maintained at 1.2 MPa. When the temperature reached 300° C. a steam flow was started at a rate of 300 ml/hr (aprox. 300 g/hr). The steam containing ε-caprolactam leaving the reactor was condensed and analyzed. After 5 hours the condensed steam contained 85.4 g ε-caprolactam. The condensed mixture was colourless on visual inspection. The yield was 99%. The autoclave was empty on visual inspection.

Example II

A horizontal tubular reactor having a volume of 100 l and equiped with a rotating axis on which mixing and scraping devices are mounted was filled, under nitrogen, with 50 kg of 6-aminocaproic acid. The reactor was furthermore equiped with means to feed steam and means to continuously feed 6-aminocaproic acid (6-ACA). Additionally at the upper side of the tube an outlet for the gaseous product was present. When the reactor was filled a steam flow of 90 kg/hr (400° C.) was started. After two hours a flow of 10 kg/hr of 60 wt. % 6-aminocaproic acid in water (90° C.) was started. The reactor temperature was maintained at 300° C. and the pressure at 1.2 MPa by using a pressure valve and additional heating.

The experiment was run for 5 hours from the moment the steam flow was started. During the experiment the gaseous outlet flow was condensed and collected. At the end of the experiment the feed of 6-aminocaproic acid was stopped.

The average concentration of ε-caprolactam in the condensate and the total amount of ε-caprolactam obtained was calculated based on the analytical data. The results are summarized in Table 1.

Example III–V

Example II was repeated in which the reaction time, feed and the steam flow were varied. See Table 1 for process conditions and results.

Example VI

Example II was repeated except that no extra 6-aminocaproic acid was fed to the reactor during the course of the experiment. See Table 1 for experimental conditions.

TABLE 1

| Exp. no. | run time (hour) | 6-ACA in Reactor (kg) start | 6-ACA in Reactor (kg) end (1) | total of 6-ACA feed (60 wt. %) to reactor (kg) | steam flow (kg/hr) T = 400° C. | total ε-caprolactam in condensate in wt % | total ε-caprolactam obtained (kg) | Conversion to ε-caprolactam (%) (5) |
|---|---|---|---|---|---|---|---|---|
| II | 5.0 | 50.0 | 11.9 | 30.2 | 90.0 | 10.1 (3) | 46.9 | 79.8 |
| III | 5.5 | 25.0 | 3.8 | 43.1 | 97.1 | 7.3 (3) | 40.1 | 91.4 |
| IV | 6.0 | 15.0 | 2.8 | 44.4 | 85.0 | 6.3 (3) | 33.1 | 92.2 |
| V (2) | 4.5 | 15.0 | 4.2 | 22.5 | 93.5 | 4.7 (3) | 20.3 | 82.6 |
| VI | 5.0 | 50.0 | 2.3 | — | 91.6 | 1.2 (4) | 40.8 | 94.6 |

(1) present as oligomers of 6-ACA
(2) 6-ACA feed contains 10% $NH_3$
(3) average concentration of ε-caprolactam in condensate in wt. %
(4) concentration after 5 hours in condensate leaving the reactor
(5) percentage of 6-ACA converted to ε-caprolactam

Example VII

Example I was repeated in which the feed, the steam flow rate and the reaction time were varied.

A reductive amination aqueous mixture containing 8.5 wt. % ε-caprolactam, 5.6 wt. % 6-aminocaproic acid, 9 wt. % 6-aminocaproic amide, 3.5 wt. % oligomers and approximately 73.4 wt. % water is concentrated by distilling off most of the water in a film evaporator.

100 g of the resulting mixture comprising 24.9 wt. % of ε-caprolactam, 16.2 wt. % 6-aminocaproic acid, 27.3 wt. % 6-aminocaproic amide, 7 wt. % oligomers and approximately 24.6 wt. % water is fed to the reactor (stirrer rate=500 rpm). The steam flow rate was 175 g/hr. The reaction time was approximately 5 hours. The yield to ε-caprolactam was >99%.

Example VIII

Example VII was repeated in which the feed was varied.

A reductive amination concentrated mixture comprising 31.2 wt. % ε-caprolactam, 24.7 wt. % 6-aminocaproic acid, 31.5 wt. % 6-aminocaproic amide, 12.3 wt. % oligomers and less than 0.3 wt. % $H_2O$ is obtained by distilling off most of the water from an aqueous reductive amination mixture, in a film evaporator. 100 g of the concentrated mixture is fed to the reactor. The yield to ε-caprolactam was >99%.

Example IX

Example I was repeated, except that the feed consisted of reductive amination mixture, and the reaction was carried out by continuously feeding an aqueous solution of reductive amination product. A 500 ml autoclave having a turbine mixer was charged with 61 grams of a mixture containing 33.9 wt. % of caprolactam, 10.9 wt. % of 6-aminocaproic acid, 38.3 wt. % of 6-aminocaproic amide, 13.6 wt. % of oligomers and 3.3 wt. % of water. After flushing with nitrogen and adjusting the pressure valve such that the pressure of the reactor was 1.2 MPa, the temperature was raised to 300° C. At the same time, the feed of a 14.2 wt % aqueous solution consisting of 4.94 wt. % of caprolactam, 1.66 wt. % of 6-aminocaproic acid, 51.70 wt. % of 6-aminocaproic amide and 1.47 wt. % of oligomers was started with a rate of 260 grams per hour. After approximately 10 hrs, the caprolactam concentration in the condensate amounted to 12.2 wt. %, which corresponds to a complete conversion of the caprolactam precursors fed, with a yield to caprolactam >99%. The reactor contents amounted approximately 100 grams. After 29 hrs. the feed rate was increased to 390 grams per hour, feeding the same mixture. Again after another 10 hrs. the caprolactam concentration in the condensed steam was 12.2 wt. %, corresponding to an almost complete conversion to caprolactam. The reactor contents in the new steady-state conditions was approximately 140 grams. The reaction was continued for a total of 54 hrs. The overall conversion of caprolactam precursors was 95%, with a selectivity of 99%;.

Example X

Example I was repeated, with the exception that the feed material was the resulting reactor contents of example IX. The steam feed rate was 390 grams per hour. After 7 hours the condensed steam contained 114 grams of caprolactam. The autoclave contained 5 grams of residue, corresponding to an overall conversion of >99.7% of the organic feed.

What is claimed is:

1. Process to prepare ε-caprolactam by treating 6-aminocaproic acid, 6-aminocaproate ester or 6-aminocaproamide or mixtures comprising at least two of these compounds in the presence of superheated steam in which a gaseous mixture comprising ε-caprolactam and steam is obtained, characterized in that the process is carried out in the absence of a catalyst at a temperature between 250 and 400° C. and at a pressure of between 0.5 and 2 MPa.

2. Process according to claim 1, characterized in that the temperature is between 270 and 350° C.

3. Process according to any one of claims 1–2, characterized in that the pressure is below 1.5 MPa.

4. Process according to claim 1, characterized in that ε-caprolactam is isolated from the gaseous mixture by partial condensation at a temperature of between 100–170° C., in which the period of time during which the gaseous mixture is cooled to the temperature of the partial condensation is within 30 seconds from leaving the reactor.

5. Process to prepare ε-caprolactam, characterized in that a mixture comprising 5–50 wt. % 6-aminocaproic acid, 10–50 wt. % 6-aminocaproamide, 0–40 wt. % ε-caprolactam, and 0–35 wt. % oligomers in which the oligomers are oligomers of ε-caprolactam, 6-aminocaproic acid and/or 6-aminocaproamide, and in which the total of all these fractions count up to 100 wt. %, is treated in a process according to claim 1.

6. Process according to claim 1, characterized in that the process is performed continuously in which steam is continuously fed to a reaction zone and in which the 6-aminocaproic acid and/or 6-aminocaproamide is continuously or semi-continuously fed to the reaction zone as aqueous mixture containing between 50–100 wt. % of these starting compounds and between 0–50 wt. % water.

7. Process according to claim 6, characterized in that the weight ratio of steam, not including any water in the feed, and the total of 6-aminocaproic acid, 6-aminocaproamide, ε-caprolactam and oligomers to the reaction zone is between 1 and 20.

8. Process to prepare ε-caprolactam starting from 6-aminocapronitrile, characterized in that (1) 6-aminocapronitrile is contacted with water under hydrolysis conditions, (2) water and ammonia, which is formed in the hydrolysis reaction, is separated and (3) the resulting mixture of (2) comprising 6-aminocaproic acid is subjected to a process according to claim 1.

9. Process according to claim 8, characterized in that the hydrolysis conditions are achieved in that a heterogeneous acid or base catalyst is present.

10. Process according to claim 9, characterized in that (1) and (2) are performed simultaneously in a reactive distillation column containing a heterogeneous acid or base catalyst in which the top product is a water/ammonia mixture and the bottom product is an aqueous mixture containing the hydrolysis products of 6-aminocapronitrile.

11. Process according to claim 8, characterized in that the hydrolysis is performed at a temperature of 250–400° C. and that any ε-caprolactam formed in the hydrolysis step (1) is separated from the other hydrolysis products by extraction prior to step (3).

12. Process according to claim 11, characterized in that the extraction is performed with a $C_5$–$C_{10}$ alcohol as extraction solvent.

* * * * *